(12) United States Patent
Thurlby

(10) Patent No.: US 8,551,473 B2
(45) Date of Patent: Oct. 8, 2013

(54) METABOLICALLY ACTIVE MICRO ORGANISMS AND METHODS FOR THEIR PRODUCTION

(75) Inventor: Timothy Thurlby, Palmerston North (NZ)

(73) Assignee: Multigerm UK Enterprises Ltd., Surrey (GB)

( * ) Notice: Subject to any disclaimer, the term of this patent is extended or adjusted under 35 U.S.C. 154(b) by 1724 days.

(21) Appl. No.: 11/663,877

(22) PCT Filed: Sep. 27, 2005

(86) PCT No.: PCT/GB2005/003715
§ 371 (c)(1), (2), (4) Date: Sep. 19, 2007

(87) PCT Pub. No.: WO2006/035218
PCT Pub. Date: Apr. 6, 2006

(65) Prior Publication Data
US 2011/0158949 A1 Jun. 30, 2011

(30) Foreign Application Priority Data

Sep. 27, 2004 (GB) ................... 0421448.2

(51) Int. Cl.
*A61K 35/74* (2006.01)
(52) U.S. Cl.
USPC .......... 424/93.4; 424/93.45; 424/93; 435/252
(58) Field of Classification Search
None
See application file for complete search history.

(56) References Cited

U.S. PATENT DOCUMENTS

| | | | |
|---|---|---|---|
| 3,623,956 A | 11/1971 | Kalabokias | |
| 3,846,397 A | 11/1974 | Ernster | |
| 4,275,164 A | 6/1981 | Masurekar | |
| 4,464,402 A | 8/1984 | Gannon | |
| 6,420,146 B1 | 7/2002 | Ramakrishna et al. | |
| 6,465,027 B1 | 10/2002 | Taillade et al. | |
| 6,811,786 B1 | 11/2004 | Farmer et al. | |
| 2002/0164399 A1 | 11/2002 | Souppe et al. | |

FOREIGN PATENT DOCUMENTS

| | | |
|---|---|---|
| EP | 0271838 | 6/1988 |
| EP | 0189657 | 6/1996 |
| GB | 906212 | 9/1962 |
| GB | 2391554 | 11/2004 |
| GB | 2418431 | 3/2006 |
| WO | 89/05849 | 6/1989 |
| WO | 97/44436 | 11/1997 |

OTHER PUBLICATIONS

Butaye et al. (Clincal Microbiol. Review, Apr. 2003, vol. 16, No. 2, pp. 175-188).*
Butaye (Antimicrobial Agents & Chemother., vol. 43, No. 10, pp. 2569-2570, Oct. 1999).*
Jaskari et al. (Appl. Microbiol. Biotechnol., 1998, vol. 49, pp. 175-181).*
Laitila et al. (Lett. in Appl. Microbiology, vol. 39, 2004, pp. 336-340).*
Wang et al. (J. Food Microbiol., vol. 93, 2004, pp. 209-217).*
Agapi et al. (Food Microbiol, vol. 27, 2010, pp. 1028-1034).*
Farooq et al. (Pak. J. Bot., vol. 44 (1), pp. 333-338, 2012).*
Suutari et al. (J. General Microbiol., 1992, vol. 138, pp. 445-450).*
Atlas, R.M. Handbook of Microbiological Media. May 21, 1993. p. 273.
Segev, D.L., et al., "Mullerian-inhibiting substance regulates NF-kappaB signaling in the prostate in vitro and in vivo," PNAS, 99(1):239-244, (Jan. 8, 2002).
Poul, M-A., et al., "Selection of tumor-specific internalizing human antibodies from phage libraries," J. Mol. Biol., 301:1149-1161, (2000).
Ishibashi, Y., "Application of ELISA to quantitative evaluation of foam-active protein in the malting and brewing process," J. Am. Soc. Brew. Chem., 55(1):20-23, (1997).
Runjic-Peric, V., et al., "Effect of glycerol as cryoprotector on the viability of mesophilic lactic acid bacteria during low temperature storage," Period Biol., 94(3):179-185, (1992).
Hassan, A.N., et al., "Factors affecting capsule size and production by lactic acid bacteria used as dairy starter cultures," Int. J. Food Microbiol., 64:199-203, (2001).
Charalampopoulos, D., et al., "Growth studies of potentially probiotic lactic acid bacteria in cereal-based substrates," J. App. Microbiol., 92:851-859, (2002).
Charalampopoulos, D., et al., "Application of cereals and cereal components in functional foods: a review," Int. J. Food Microbiol., 79:131-141, (2002).
Charalampopoulos, D., et al., "Evaluation of the effect of malt, wheat and barley extracts on the viability of potentially probiotic lactic acid bacteria under acidic conditions," Int. J. Food Microbiol., 82:133-141, (2003).
Laitila, A., et al. "Malt sprout extract medium for cultivation of *Lactobacillus plantarum* protective cultures." Lett Appl Microbiol. 2004;39(4):336-40.

* cited by examiner

*Primary Examiner* — Hope Robinson
(74) *Attorney, Agent, or Firm* — Dann, Dorfman, Herrell & Skillman; Kathleen D. Rigaut

(57) ABSTRACT

The invention relates to a preparation of metabolically active bacteria, compositions comprising such a preparation, e.g., probiotic supplements or animal feeds, and to uses thereof, for example in the treatment of diseases affecting the intestinal microbial balance. Also described are a growth substrate for microorganisms comprising a mixture of complex and simple sugars and a process for the manufacture of preparations of metabolically active microorganisms using this growth substrate.

8 Claims, 3 Drawing Sheets

METABOLICALLY ACTIVE MICRO ORGANISMS AND METHODS FOR THEIR PRODUCTION

This application is a §371 application of PCT/GB2005/003715, filed 27 Sep. 2005, which in turn claims priority to GB 0421448.2 filed 27 September 2004, the entire disclosure of which is incorporated by reference herein.

FIELD OF THE INVENTION

The invention relates to a preparation of metabolically active bacteria, compositions comprising such a preparation, e.g. probiotic supplements or animal feeds, and to uses thereof, for example in the treatment of disease. The invention also relates to a growth substrate for microorganisms comprising a mixture of complex and simple sugars and to a process for the manufacture of preparations of metabolically active microorganisms using this growth substrate.

BACKGROUND TO THE INVENTION

Microbiological organisms are frequently used as food supplements. One example are probiotic bacteria which are known to have beneficial effects on the intestinal microflora increasing the resistance to infectious disease such as diarrhea. Probiotics have also been shown to be involved in the modification of blood chemistry and in immunomodulation (see references listed under Potential Health Benefits in the reference section).

Probiotic bacteria can be found in dairy products such as yogurt and species known to have health benefits include those from the genera Enterococcus and Lactobacillus. However, probiotic dairy products have a short shelf life. Probiotics are also available to the consumer in form of powder or tablets. A further application of probiotics relates to use in animal feed.

Current methods for storing bacterial cultures typically use lyophilization, also called freeze-drying. In this process, water is removed from the organism by sublimation and the organism and can be revived after the addition of water. However, freeze-dried bacteria are not metabolically active and it is well known that freeze-dried products typically lose much of their resilience after a few weeks of storage at room temperature (Fonseca et al and Murga et al).

Furthermore, many commercial probiotics do not seem to contain all of the species mentioned on the labels, and where bacteria are present the numbers of viable bacteria are often very low (J. Hamilton-Miller).

The present inventors have now determined that stable preparations of viable, metabolically active bacteria can be prepared by use of a particular growth substrate which contains balanced amounts of complex and simple carbohydrates. In contrast to prior art probiotics, the preparations provided according to the present invention comprise high numbers of stable and active bacteria which can be maintained during long term storage.

DESCRIPTION OF THE INVENTION

In accordance with a first aspect of the invention there is provided a preparation comprising viable, metabolically active bacteria and a growth substrate comprising a mixture of complex and simple carbohydrates wherein the bacteria exhibit a equilibrium growth state characterised in that the population of bacteria is maintained at a constant level when stored at about 4° C. and at controlled pH for a period of at least 5 months.

It is an essential feature of the invention that in this preparation, the bacterial culture can be maintained in an equilibrium state for a period of at least 5 months at 4° at controlled pH. In this state, the bacterial multiplication rate is maintained close to the death rate. In a preferred embodiment, the population of metabolically active bacteria in the near equilibrium state is maintained in the range of from $10^8$ to $10^9$ viable cells per millilitre.

The growth substrate comprises a mixture of complex and simple carbohydrates (sugars). As used herein the terms "complex carbohydrates" or "complex sugars" include oligosaccharides and polysaccharides, whereas the terms "simple carbohydrates" or "simple sugars" include monosaccharides and disaccharides.

Preferably, the total amount of sugars in the growth substrates is in the range of from 20 mg/ml to 40 mg/ml and the total amount of reducing sugars is in the range of from 5 mg/ml to 20 mg/ml. In a preferred embodiment, the concentration of total sugars is about 30 mg/ml and the concentration of reducing sugars is about 10 mg/ml.

The growth substrate preferably also comprises protein and peptide components. Typically the total amount of protein and peptides present in the substrate is in the range of from 1 mg/ml to 2 mg/ml and the total amount of high molecular weight peptides (molecular weight greater than 5000 Daltons) is in the range of from 100 μg/ml to 300 μg/ml. In a specific embodiment, the concentration of protein and peptides may be about 2 mg/ml and the concentration of high molecular weight peptides may be about 250 μg/ml.

The growth substrate may contain further components such as, for example, cellulose, starch, β-glucans, pentosans, polyphenols, ribonucleic acids, lipids, phosphates, flavenoids, amino acids, vitamins ($B_1$, $B_2$, C and E), silicates and trace elements.

In a preferred embodiment the growth substrate is derived from malted cereal grains. Most preferably the growth substrate is prepared using the process described hereinbelow.

The invention presents an advantage over current probiotic preparations as metabolically active bacteria can be stored for a number of months without deterioration or loss of activity. Preparations of freeze-dried bacteria which are currently used typically contain few, if any, metabolically active bacteria. Furthermore, preparations of freeze-dried bacteria lose some of their characteristics and activity upon rehydration. Also, the reactivated bacteria have a short shelf life and can be kept in storage for a short time only. Freeze-dried bacteria are often not rehydrated before use in a host animal. If they are rehydrated, then they generally have to be used on the same day, otherwise there may be rapid loss in viability and spoilage from contaminating organisms.

A further problem with prior art freeze-dried preparations is that they are hygroscopic (attract moisture from the air) and therefore a packet has to be used within a few days of opening, otherwise the partial hydration will cause rapid loss of viability.

The preparation according to the invention avoids the above-listed problems associated with the use of freeze-dried bacterial cultures. In addition, it has also been shown by the inventors that the bacterial cultures prepared according to the invention are significantly more robust than bacteria prepared by methods known in the prior art, which enables the bacteria to establish more rapidly in host animals and to tolerate the harsh environment of the mammalian digestive tract (illustrated in example 5).

The inventors have overcome the problems of conventionally used preparations by using a growth substrate with balanced nutrient supply in the form of complex and simple sugars, proteins and peptides in combination with controlled pH and cold storage. Under these conditions there is a continuous slow growth of bacteria in the preparation. The combination of temperature, pH, phase growth and substrate imposes a near equilibrium growth state, whereby high concentrations of viable, metabolically active bacteria can be maintained for periods of at least 5 months.

In one embodiment, the pH of the preparation when stored is maintained in the range of from 3.8 to 4.5. In a specific embodiment the pH of the preparation is maintained at about 4.0 during storage. The pH of the preparation can be conveniently controlled by the addition of a suitable buffer or combination of buffering agents. Preferred buffers include, for example, tri-sodium citrate or phosphate buffers. The use of buffers, such as tri-sodium citrate or phosphate buffers is described in standard methods in the art.

In a preferred embodiment, the bacteria in the preparation are lactic acid bacteria. The term "lactic acid bacteria (LAB)" as used herein described a group of Gram positive, catalase negative, non-motile anaerobic bacteria that ferment carbohydrates to lactic acid. This group includes the genera *Lactobacillus, Lactococcus, Pediococcus, Bifidobacterium,* and *Enterococcus.*

In a preferred embodiment, the bacteria are of the genus *Lactobacillus* or *Enterococcus*. In the most preferred embodiment, the lactic acid bacteria are of at least one of the following species: *Enterococcus faecium, Lactobacillus plantarum, Lactobacillus casei* and *Lactobacillus acidophilus*. In a preferred embodiment, a combination of *Enterococcus faecium, Lactobacillus plantarum, Lactobacillus casei* is used.

The preparation may additionally comprises an anti-fungal agent, such as, for example, sterilised potassium sorbate and/ or and anti oxidant, such as vitamin C.

In a second aspect the invention also provides a growth substrate for microorganisms (especially bacteria) comprising a complex mix of carbohydrates. The growth substrate comprises a mixture of complex and simple sugars, including sugar monomers, dimers, oligomers and polymers.

The preferred features of the growth substrate are substantially as described above in relation to the first aspect of the invention. Thus, the total amount of carbohydrate (simple plus complex sugars) present in the growth substrate is preferably in the range of from 20 mg/ml to 40 mg/ml, more preferably in the range of from 25 mg/ml to 35 mg/ml and is most preferably about 30 mg/ml. Of this total carbohydrate (sugar) content, the total amount of reducing sugars (monosaccharides) is preferably in the range of 5 mg/ml to 20 mg/ml, more preferably from 5 mg/ml to 15 mg/ml and most preferably about 10 mg/ml.

While simple and complex carbohydrates are the key component of the growth substrate, it will be appreciated that the growth substrate may also contain further components, such as proteins which provide nitrogen for bacterial growth. Accordingly, the growth substrate preferably comprises a total amount of protein and peptides in the range of from 1 mg/ml to 2 mg/ml, preferably about 2 mg/ml. Of this total protein/peptide content the total amount of high molecular weight peptides (molecular weight greater that 5000 Daltons) may be in the range of from 100 µg/ml to 300 µg/ml, and typically about 250 µg/ml. The precise identity (e.g. amino acid sequence) of the protein and peptide components in the growth substrate is generally not material to the invention.

The growth substrate may contain further components such as, for example, cellulose, starch, β-glucans, pentosans, polyphenols, ribonucleic acids, lipids, phosphates, flavenoids, amino acids, vitamins ($B_1$, $B_2$, C and E), silicates and trace elements. The precise identity and relative quantities of these additional components in the substrate is not particularly limiting. If, as is preferred, the growth substrate is derived from a natural plant source, for example malted cereal grains, these further components will usually be naturally occurring biomolecules.

The growth substrate may contain various additives such as buffering agents and other substances designed to improve the performance of the substrate and/or to extend shelf-life. Such additives may include, for example, anti-fungal agents, anti-oxidants etc.

In a preferred embodiment the growth substrate may contain particulate matter, for example particles not exceeding 1 mm in diameter.

The growth substrate may be prepared starting from malted cereal grains using the manufacturing process described hereinbelow. However, the invention is not intended to be limited to substrates prepared according to this process. Growth substrates exhibiting substantially similar properties may be prepared synthetically, for example by mixing together the required mixture of complex and simple carbohydrates, together with any of the additional components listed above.

According to a further aspect of the invention, there is provided a method for preparing a growth substrate for micro organisms comprising:

subjecting malted cereal to a mashing step in which the malted cereal is mixed with aqueous liquid and subjected to conditions of time and temperature which limit the extent of conversion of complex to simple carbohydrates such that a mixture of complex and simple carbohydrates, proteins and peptides is obtained, and separating the mixture of complex and simple carbohydrates, proteins and peptides from the spent malted cereal to obtain a growth substrate.

The terms "malted cereal" or "malt" as used herein refers to the product of a malting process applied to cereal grains. Malting is a process well known in the art of brewing.

In a typical malting process cereal grains are germinated to induce the mobilization of storage nutrients. Germinating seeds produce a number of enzymes to mobilize storage proteins and carbohydrates, including α-amylases which hydrolyse starch into maltose. A preferred embodiment relates to the use of barley, but other cereals, such as rice, wheat, corn and oats or even mixtures thereof, may be used within the scope of the invention. The process of germination is generally well known. It will be appreciated that the method may be carried out by providing malted grains or a synthetic substrate comprising a mixture of carbohydrates, proteins and enzymes.

Preferably, the malting grains are rolled before further processing. Cracking of the grains by rolling facilitates access of water and extraction of nutrients during the mashing step, whilst avoiding shattering of the grains assists in the subsequent separation of the growth substrate from spent malted grains.

The prepared malt is subjected to a mashing step which resembles the mashing-in step used in methods for brewing (see, for example, Kunze, W. Technology Brewing and Malting (1996)). The term "mashing-in" is well known in the field of brewing and relates to a process wherein malted grains are agitated in the presence of water heated to defined temperatures in order to prepare a wort. During the mashing in step complex carbohydrates in the malted grains are broken down into maltose.

The method of the invention also involves a mash step in which malted cereal grains are mixed with an aqueous liquid (typically water) and the mixture heated to various defined temperatures. This mash step does not, however, conform to a typical brewer's mashing-in process. Brewers aim to convert as much carbohydrate to simple sugars as possible, for subsequent fermentation to alcohol. In contrast, the conditions of the mash step in the process of the invention are specifically chosen to limit the extent of conversion to simple (reducing) sugars, leaving significant amounts of carbohydrates in more complex oligomeric and polymeric forms.

In non-limiting embodiments the extent of conversion of carbohydrate may be limited such that the amount of simple (reducing) sugars present in the resulting growth substrate, expressed as a percentage (w/w) of total carbohydrate content is in the range of from 10% (w/w) to 50% (w/w).

The desired limited conversion of complex to simple sugars may be achieved by increasing the temperature in the mash step over a short period of time, typically 30 minutes, without allowing the mixture of malted grains/water to rest at intermediate temperatures. Traditional brewing processes include rests at 60-65° C. and 70-74° C., as this allows enzymes to produce high concentrations of simple sugars (mainly maltose). Accordingly, in a preferred embodiment of the invention, the mashing-in step does not comprise rests at temperatures in the range of from 60° C. to 65° C. and/or at temperatures in the range of from 70° C. to 74° C.

In a specific embodiment, the mash step comprises mixing the malted cereal with water at a temperature in the range of from 30° C. to 45° C., resting the mixture for 1 to 2 hours, increasing the temperature to a temperature in the range of from 75° C. to 85° C. over a time period in the range of from 20 to 40 minutes, preferably 30 minutes, and then resting the mixture at a temperature in the range of from 75° C. to 85° C. for a period of time in the range of from 60 to 90 minutes. At the higher temperature, any enzymes present in the mixture are inactivated and nutrients can be extracted. Higher temperatures in the range of from 76° C. to 80° C. and specifically 78° C. are generally preferred. The temperature in this step needs to be sufficiently high for sufficiently long to inactivate all enzymes present in the preparation. It will be appreciated that the precise temperature and times used can vary somewhat according to the type of cereal used.

The process described here specifically limits the amount of conversion of complex sugars to simple sugars. Furthermore, the initial rest at a temperature in the range of from 30° C. to 45° C. provides an additional advantage in that it maximises the release of amino acids and peptides. Temperatures towards the higher end of this range, i.e. from 40° C. to 45° C. qr specifically about 45° C., are generally preferred. The purpose of this step is to hydrolyse storage proteins present in the cereal grains into available amino acids and peptides. The optimum combination of time and temperature to achieve the desired hydrolysis may vary somewhat depending on the type of grains used.

The presence of high concentrations of proteins, peptides and amino acids is desirable in a growth substrate to be used to support the growth of microorganisms as it provides a useful a source of nitrogen. Typical mashing-in processes used in traditional brewing would generally not include a rest at a temperature in this range, since brewers do not normally seek to achieve high protein or amino acid content in a wort intended for fermentation to produce alcohol.

When the mash step is complete, e.g. all the desired nutrients have been extracted from the now "spent" malted grains, the resulting mixture comprising complex and simple carbohydrates, proteins and peptides may be separated from the spent grains to obtain a growth substrate using any suitable means. Typically this will involve coarse filtration, for example using a 1 mm filter such as a wedge-wire basket, yielding a solution containing coarse particles. It is a feature of the process of the invention that the growth substrate is not clarified, as would generally be the case with a wort prepared during standard brewing. In traditional brewing the wort is generally clarified to remove all coarse particles, thereby producing a clear liquid.

The presence of some particulate matter in a growth substrate prepared according to the process of the invention is advantageous as regards subsequent use in supporting the growth of bacteria since it provides both slow release nutrients and particulate surfaces for the adhesion of bacterial cultures.

If required, the growth substrate prepared according to the invention can be sterilized prior to further usage. As will be appreciated, this can be carried out by boiling for about one hour or by autoclaving at 120° C. for about 20 minutes.

A buffer, or several buffering components may be added to the growth substrate if required, for example if the growth substrate is to be subsequently used in the manufacture of a bacterial preparation according to the first aspect of the invention. Preferred buffers are as listed in connection with the first aspect of the invention. If the growth substrate is to be sterilized, the buffer(s) may be added prior to, during or after sterilization as convenient.

In a further aspect the invention also relates to a method of producing viable, metabolically active and stable micro organisms comprising:
  growing micro organisms in a growth substrate comprising a mixture of complex and simple sugars, proteins and peptides to obtain a preparation of microorganisms, and
  chilling the resulting preparation to about 4° C. wherein the micro organisms adopt a near equilibrium growth state characterized in that the population of bacteria in the preparation can be maintained at a constant level when stored at about 4° C. and at controlled pH for a period of at least 5 months, and optionally storing the preparation at about 4° C.

In a preferred embodiment of this method the microorganisms are bacteria.

In a specific embodiment, the bacteria are grown in the growth substrate until they reach a concentration of between $2 \times 10^8$ and $1 \times 10^9$ colony forming units per millilitre. At this point the culture (or fermentation) is cooled down to about 4° C. and the combination of temperature, pH, phase of growth and residual substrate composition provides the equilibrium conditions which allows for maintenance of a near equilibrium growth state during long term storage. In this near equilibrium state, which can be maintained for a period of at least 5 months, the population of metabolically active bacteria is maintained at a substantially constant level in the range of from $10^8$ to $10^9$ viable cells per millilitre. It will be appreciated, however, that the precise number of viable cells at the near equilibrium state can vary somewhat depending on the species of bacteria used.

The method according to this aspect of the invention involves a "growing step" in which the microorganisms (e.g. bacteria) are grown in a growth substrate until they reach a concentration which enables the near-equilibrium condition to be achieved during subsequent storage. It is an important feature of the method that the growth substrate used provides a balanced nutrient supply containing a mixture of complex and simple sugars wherein a high proportion of carbohydrate content is in the form of complex sugars that may be used as an energy source by the micro organism. This mix helps to Limit immediately available energy during the growing step. The composition and preferred features of the growth substrate is/are preferably as described above in connection with the first and second aspects of the invention. The growth substrate is preferably prepared from malted cereal grains using the manufacturing method described herein. It will be appreciated, however, that it is not strictly necessary to use growth substrate prepared according to this method. Similar results can be achieved using growth substrate prepared synthetically by mixing the required proportions of complex and simple carbohydrates, proteins and peptides.

The growing step must be carried out in such a way that care is taken not to grow the micro organisms for too long, to avoid producing acid conditions which would otherwise inhibit further growth as well as limiting the period of storage of the resulting preparation. On the other hand, if the growing step is terminated prematurely, this will limit biomass production. The pH of the preparation during growth of the micro organisms can be used as an indicator of the near equilibrium state. In a typical embodiment, cultures of lactic acid bacteria may be grown until a pH of 4.5±0.3 units is reached.

It will be appreciated that the pH of the growth substrate may vary somewhat depending on the optimal pH range for the micro organism (e.g. bacteria) used. In a typical embodiment (suitable for lactic acid bacteria) pH should be maintained in the range of from 3.8 to 4.5 during storage. Preferably buffers, such as tri-sodium citrate or phosphates are added to the growth substrate to control the pH during growth of the micro organisms and subsequent storage.

It will be appreciated that the exact timing of the step of growing the micro organisms (e.g. bacteria) to a near equilibrium state depends on the species used. Growth of the micro organisms can be carried out in any suitable culture apparatus. In specific embodiments the growing step can be carried out by way of fermentation in a fermentation vessel.

In a preferred embodiment, the micro organisms used are lactic acid bacteria. Preferred species are of the genera *Enterococcus* and *Lactobacillus*. If such species were to be grown using "conventional" growth media consisting largely of simple sugars the excess energy supply would lead to excess acid production by lactic acid bacteria, which would limit biomass production and shelf life of the resulting culture. In contrast, the complex mix of sugars present in the growth substrate used in the method of the invention supplies energy for growth in the initial growing step and also for maintenance during storage of the product.

According to the invention, the growing step can be carried out using a single species of bacteria (or other microorganism). In a preferred embodiment of the invention, two or more different bacterial (microorganism) species may be grown independently in separate growth media and then blended together before or after the chilling step. The growth substrates used for independent culture of two or more different bacterial species may be the same or of different composition. Thus, it is possible to optimise the growing conditions for cultures of individual bacterial species and then combine the cultures together for storage under conditions which permit maintenance of equilibrium growth for each of the individual species in the culture.

In other embodiments of the method two or more different bacterial species (or other microorganisms) can be grown together in a single culture in the same growth substrate, provided that their growth rates are comparable so that one species does not dominate the population. Following the growing step, the preparation can be analyzed by standard methods to determine the microbiological purity and enumeration of micro organisms. It is also possible to grow two or more different combinations of microorganisms (e.g. bacteria) together in separate growth substrates and then combine the cultures together in a final product. A combination culture could similarly be blended with a culture of a single bacterial species.

In other embodiments of the method two or more different bacterial species (or other microorganisms) can be grown together in a single culture in the same growth substrate, provided that their growth rates are comparable so that one species does not dominate the population. Following the growing step, the preparation can be analysed by standard methods to determine the microbiological purity and enumeration of micro organisms. It is also possible to grow two or more different combinations of microorganisms (e.g. bacteria) together in separate growth substrates and then combine the cultures together in a final product. A combination culture could similarly be blended with a culture of a single bacterial species.

Starter cultures for the growing step of the method include, for example, freeze-dried bacteria or liquid cultures.

It will be appreciated that the preparation of microorganisms prepared using the method of the invention may be used immediately after the chilling step but more typically the preparation will be stored before use. The optimum temperature for storage in order to maintain the near equilibrium growth state in the culture is about 4° C. but it will be appreciated by the skilled reader that the storage temperature could vary somewhat. For convenience, aliquots of the near-equilibrium culture produced by the method may be dispensed into suitable sterile packaging prior to long term storage.

It is a key advantage of the method of the invention that the near-equilibrium cultures produced maintain viability and integrity when stored for extended periods, typically for at least 5 months. However, it will be appreciated that it is not essential to the method that the cultures must actually be stored for at least 5 months prior to use.

To avoid the growth of fungi or yeast, an anti fungal agent, such as sterile potassium sorbate, may be added prior to storage. The anti fungal agents are primarily to prevent spoilage by yeast or fungi during use by end-users, once a container of the product has been opened. Furthermore, an anti oxidant, for example, vitamin C can be added to help to prevent spoilage of the product during storage. It will be appreciated that other agents well known in the art can also be used as anti fungal agents or anti oxidants.

In a further aspect the invention also relates to an alternative method of producing a preparation of viable, metabolically active and stable micro organisms which does not require an active growing step. This method comprises the following steps: adding microorganisms to a growth substrate comprising a mixture of complex and simple sugars, proteins and peptides to form a preparation of microorganisms, wherein the microorganisms are added to the growth substrate at a concentration providing a near equilibrium growth state characterized in that the population of microorganisms in the preparation can be maintained at a constant level when stored at about 4° C. and at controlled pH for a period of at least 5 months, and optionally storing the preparation at about 4° C.

In a preferred embodiment of this method the microorganisms are bacteria. Preferred bacterial species are as listed above in connection with the method requiring an active growing step.

This method does not require the microorganisms (e.g. bacteria) to be grown in the growth substrate before the conditions for near-equilibrium growth are imposed. Rather, the growth substrate is inoculated with starter culture(s) of microorganisms (e.g. bacteria) at a concentration that will allow for the maintenance of the equilibrium state when the resulting preparation is stored at 4° C. and at controlled pH for a period of at least 5 months. Starter cultures for the method include, for example, freeze-dried bacteria or liquid cultures. The growth substrate may be inoculated with more than one bacterial species. Preferably, the concentration of the viable cells in the starter culture is in excess of $10^8$ viable cells per millilitre.

The near equilibrium state is again achieved by the combination of nutrients in the growth substrate, temperature, pH and phase growth. In the near equilibrium state, which can be maintained for a period of at least 5 months, the population of metabolically active bacteria is preferably maintained at a constant level in the range of $10^8$ to $10^9$ viable cells per millilitre. Again it will be appreciated that the precise number of viable cells at the near equilibrium state can vary somewhat depending on the species of bacteria used. It will also be appreciated that the exact concentration of the starter culture and pH of the growth substrate may vary depending on the species of bacteria used.

Features described as preferred in relation to the near-equilibrium cultures produced using the method requiring a growing step apply mutatis mutandis to the near-equilibrium cultures achieved using this method. Thus, in a preferred embodiment, the pH of the near-equilibrium culture is maintained in the range of from 3.8 to 4.5 during storage. Preferably buffers, such as tri-sodium citrate or phosphates, are used to control the pH during storage.

In a preferred embodiment, the micro organisms used are lactic acid bacteria. Preferred species are of the genera *Enterococcus* and *Lactobacillus*.

Preferred features of the growth substrate used in this method are as described above in relation to the second aspect of the invention. Again, it is preferred but not essential that the growth substrate be prepared from malted cereal grains using the process described herein.

Uses of the Preparation of Metabolically Active Bacteria

The health benefits of probiotics are well known (see, for example, Marteau, P. and Rambaud, J-C, (1996) 'Therapeutic applications of probiotics in humans' in Leeds, A. R. and Rowland, I. R. (eds.) Gut flora and health—past, present and future, Royal Society of Medicine Press Limited, London; Stark, B. A. and Wilkinson, (eds.) (1989) *Probiotics. Theory and Applications*). Probiotics have shown to be useful in the treatment of diarrhea and constipation, irritable bowel syndrome, cancer treatment and prevention and other diseases affecting the intestinal microflora.

The bacterial preparations provided by the invention therefore find particular utility in the treatment or prevention of diseases that affect the microbial intestinal flora, and more general utility in helping to maintain a healthy microbial flora.

Thus, in a further aspect the invention provides a method of treating or preventing a disorder affecting the intestinal microbial balance in a human or animal patient comprising administering to a patient in need thereof an effective amount of a metabolically active and stable preparation of bacteria according to the invention.

In particular, the invention relates to the treatment or prevention of chronic inflammatory bowel disease, ulcerative colitis or Crohn's disease. Furthermore, the bacterial cultures according to the invention can be administered to human or animal (e.g. mammalian or avian) patients for general maintenance of a healthy microbial flora, rather than for treatment of a specific disease.

In a further embodiment the invention also relates to the use of a metabolically active and stable preparation of bacteria according to the invention in the manufacture of a medicament for the treatment of diseases that affect the microbial intestinal flora.

The bacterial preparations may be used as they are, for example as probiotic supplements, or they may be admixed with further components prior to administration to a human or animal subject, or even administered together with further components without admixture. For veterinary use it may be convenient to add the bacterial preparation to normal animal feed. In the veterinary field the preparations find particular utility in the treatment of avian species, especially commercial poultry (as illustrated in the accompanying examples), as well as mammalian species, e.g. cows, sheep, horses, cats, dogs etc.

For human use the bacterial preparations may be administered as they are or may again be admixed or formulated with additional components prior to administration to a human subject. The invention thus encompasses compositions comprising a bacterial preparation according to the invention plus one or more further components. By way of example, additional components may be added to improve the palatability of the composition for human consumption. If convenient, the preparations according to the invention may be incorporated into foodstuffs or beverages for human consumption, provided that this does not affect the viability of the bacteria in the preparation.

For human and/or veterinary use it may be convenient to formulate the preparations according to the invention into unit dosage forms, either alone or in combination with one or more pharmaceutically acceptable diluents, excipients or carriers. Again such formulation should not adversely affect the viability of the bacteria in the preparation.

BRIEF DESCRIPTION OF THE DRAWINGS

FIG. 1*d* shows the growth of *Lactobacillus plantarum* prepared by the method described herein ("wet") compared to a lyophilised preparation of the bacterium ("dry") at a low pH and in the presence of bile salts simulating an environment as found in the digestive tract of mammals. The results show that the bacteria prepared according to the method of the invention are more resistant to a hostile environment.

Figure 1A:
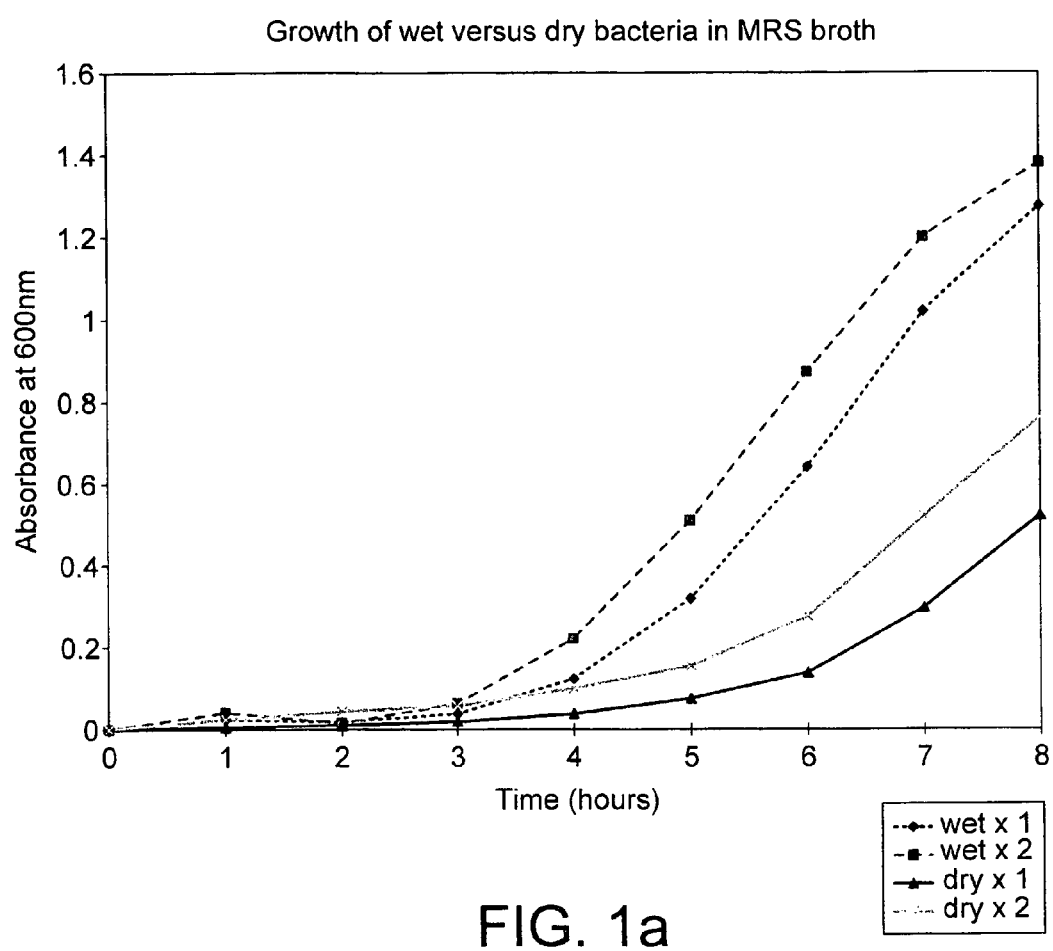
FIGS. 1*a*-1*d* show the robustness of a liquid culture of *Lactobacillus plantarum* prepared by the method described herein ("wet") compared to a lyophilised preparation of the bacterium ("dry"). The first two growth curves (FIGS. 1*a* and 1*b*) indicate that in a non-hostile environment, the bacteria prepared according to the invention grow faster than the lyophilised preparation. The growth curve in FIG. 1*c* shows the growth of *Lactobacillus plantarum* prepared by the method described herein ("wet") compared to a lyophilised preparation of the bacterium ("dry")in a medium supplemented with bile salts.

The invention will be further understood with reference to the following non-limiting experimental examples.

EXAMPLE 1

Production of a Growth Substrate, using a Barley-Based Medium (A) Germination (Malting)

Day 1

Barley was steeped in water for 2 to 24 hours, depending on the batch of grain. 0.1% (w/v) sodium hypochlorite (bleach)

can be included in the water to inhibit growth of contaminants during the germination phase. After 4 hours, the water was drained from the grains and the grains left to stand at room temperature from 10 to 30 °C. for approximately 1 day.

Day 2

The grains were steeped in clean water for another 4-hour period. Hydrogen peroxide (0.1% w/v) may be added to the water for this and subsequent soaks. Hydrogen peroxide providse oxygen for the germinating grains, and act as a disinfectant. Alternatively, sodium hypochlorite may be used. After 4 hours, water was drained from the grains and the grains left to stand for approximately 1 day. Occasional (e.g. every 4 hours) agitation of the grains may improve germination by increasing gaseous exchange, providing oxygen and removing carbon dioxide.

Day 3 onwards

The cycle of steeping, draining and standing was continued until the emerging rootlets on the germinating grains were 2 to 4 mm long. This state of growth indicated that the grains had produced enzymes for the mobilisation of stored nutrients. These enzymes are central to the subsequent production of the growth medium, during 'mashing-in.' More extensive modification of the grains could be allowed, leaving the germination phase until the rootlets are several millimetres long. However, too much growth will merely convert nutrients into plant roots and shoots, which cannot be used in the fermentation.

(B) Rolling

When the grains had germinated sufficiently, they were then milled with a roller mill. The mill was adjusted such that the grains were cracked open but not shattered or completely flattened. Cracking of the grains allows access of water and extraction of nutrients during mashing in, whilst avoiding shattering of the grains assists in filtration steps.

(C) Preparation of a Growth Substrate.

The germinated, milled, grains were mixed with sufficient water to cover-them, at 45° C., and the mixture held at 45° C. for 1 hour.

After 1 hour at 45° C., the temperature was increased to 78° C. over a period of 30 minutes.

The mixture was allowed to stand at 78° C. for 1 hour. After the 78° C. stand, the spent grains were separated out by filtration. A relatively coarse filter (e.g. 1 mm gap wedge-wire basket) was used yielding a solution containing significant amounts of suspended solids. The spent grains were discarded and the liquid then heat-treated to pasteurize or sterilize it. In this particular experiment the liquid was boiled for 45 minutes. A buffer (0.5% (w/v) tri-sodium citrate) was then added and the mixture boiled for a further 15 minutes to yield the final growth substrate.

EXAMPLE 2

Analysis of the Growth Substrate (a) Carbohydrate Analyses:

Total carbohydrate content was determined using the phenol-sulphuric acid assay, with glucose as reference standard. (Dubois, M., Gilles, K. A., Hamilton, J. K., Rebers, P. A. and Smith, F. (1956) *Analytical Chemistry*, vol. 28., p. 350).

Reducing sugars were determined using the Nelson-Somogyi method, again with glucose as the reference standard. (Somogyi, M. (1952) Journal of Biological Chemistry., vol. 195., p. 19).

Results:

Total sugars in substrate are in the range 20 to 40 mg/ml (milligrams per millilitre)

Reducing sugars are in the range 5 to 20 mg/ml.

(b) Protein and Peptide Analyses:

Total protein was determined using two assays, with bovine serum albumin as reference standard:
(i) The Biuret Reagent (Itzhaki, R. F & Gill, D. M. (1964) Analytical Biochemistry, Vol. 9., p. 401-410.
(ii) The Lowry Method, as modified by Ohnishi and Barr. (Ohnishi, S. T. & Barr, J. K. (1978) Journal of Biological Chemistry, Vol. 193, p. 265).

Peptides of molecular weight above 5000 daltons were determined using the Bradford Reagent (Bradford, M. M. (1976) Analytical Biochemistry, Vol. 72, p. 248-254).

Results:

Total protein and peptides are in the range 1 to 2 milligrams per millilitre.

High molecular weight peptides (greater than 5000 daltons) are in the range 100 to 300 micrograms per millilitre.

EXAMPLE 3

Production of a Metabolically Active Bacterial Culture (A) Fermentation

The growth substrate prepared according to example 1 was cooled to 37° C. and the bacterial cultures added. Examples of a suitable inoculum are freeze-dried bacteria or liquid starter cultures (typically 1% (v/v) of an overnight culture in nutrient broth).

In this example the following bacteria were grown in two vessels:
(i) *Enterococcus faecium, Lactobacillus plantarum;*
(ii) *Lactobacillus casei*

Fermentation was carried out for 16-20 hours, until the pH reached 4.5±0.3 units. The fermentation mixture was then cooled to 4° C. and subjected standard techniques to assess quality (to determine microbiological purity and enumeration of bacteria).

At this point, sterile potassium sorbate (0.005% w/v final concentration) may be added to the fermented broth. This acts to inhibit the growth of any fungi or yeast that may arise due to contamination during handling by the end-user.

Vitamin C may also be added (0.01% w/v final concentration) as an anti-oxidant.

Following quality assurance tests, different batches can be blended to give products with complex mixtures of bacterial species, if required.

In the example presented here, blending of the two batches of bacteria yielded a final product containing the bacteria *Enterococcus faecium, Lactobacillus plantarum* and *Lactobacillus casei*.

EXAMPLE 4

Shelf Life of the Metabolically Active Bacterial Culture

To assess the shelf life of the metabolically active bacterial culture, batches of the bacterial culture comprising the species *Enterococcus faecium, Lactobacillus plantarum* and *Lactobacillus casei*, as obtained in example 2 were stored at 4° C. (±1° C.). Samples were taken at weekly intervals, and 100 ul aliquots of serial dilutions in 0.1% (w/v) peptone water were spread on agar plates. The plates were incubated for about 48 hours at about 37° C. and the bacterial colonies counted.

Results

Figure 2A:
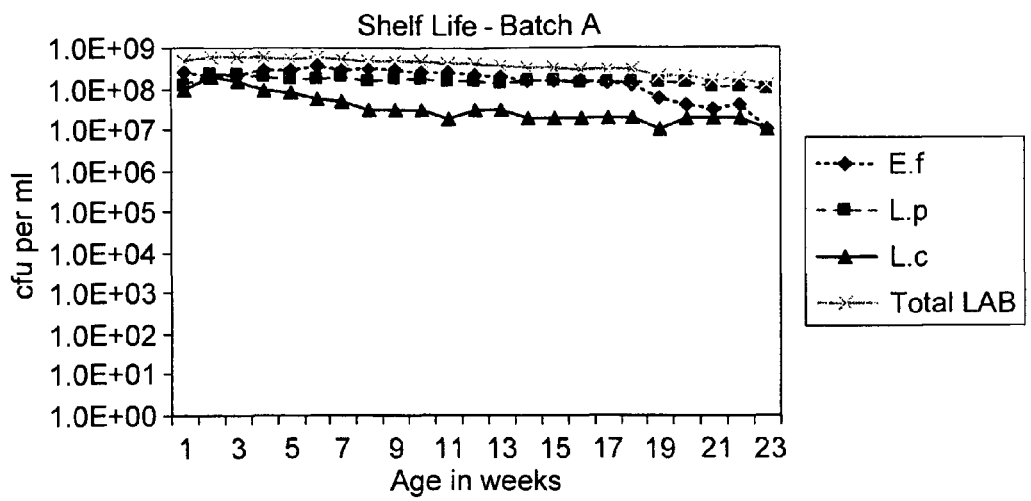
FIGS. 2*a* and 2*b* show that the shelf life of bacteria prepared according to the invention is increased.
Figure 2B:
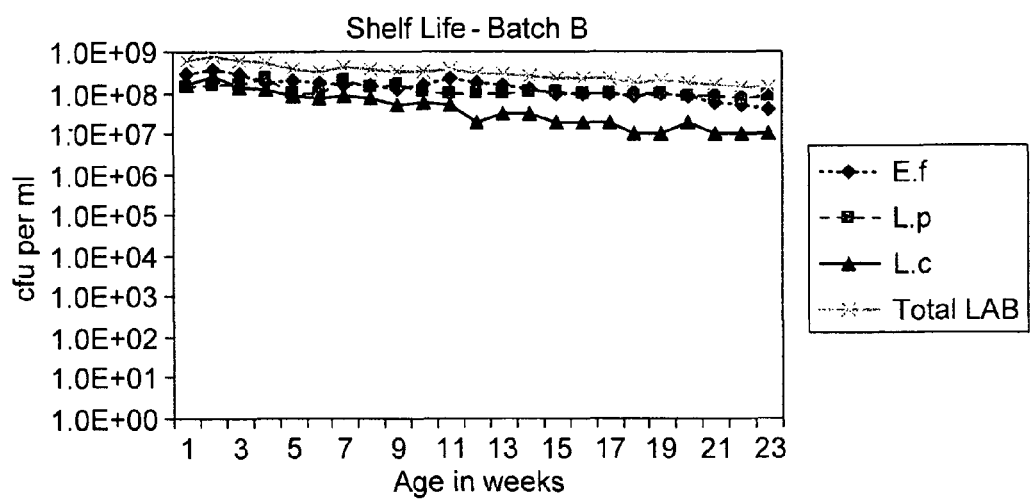

The results below show the shelf life for bacteria prepared by the method of the invention as number of colony forming units per millilitre per week (also see FIG. 2). Batch A and B have been prepared according to the same method as described herein but on different days.

TABLE 1

Batch A (8059)

| Week | E.f | L.p | L.c | Total LAB |
|---|---|---|---|---|
| 0 | 2.7E+08 | 1.2E+08 | 9.0E+07 | 4.8E+08 |
| 1 | 2.0E+08 | 2.4E+08 | 1.9E+08 | 6.3E+08 |
| 2 | 2.4E+08 | 2.2E+08 | 1.5E+08 | 6.1E+08 |
| 3 | 3.0E+08 | 1.9E+08 | 9.0E+07 | 5.8E+08 |
| 4 | 3.0E+08 | 1.8E+08 | 8.0E+07 | 5.6E+08 |
| 5 | 3.5E+08 | 1.7E+08 | 6.0E+07 | 5.8E+08 |
| 6 | 3.0E+08 | 1.9E+08 | 5.0E+07 | 5.4E+08 |
| 7 | 3.1E+08 | 1.5E+08 | 3.0E+07 | 4.9E+08 |
| 8 | 2.8E+08 | 1.7E+08 | 3.0E+07 | 4.8E+08 |
| 9 | 2.5E+08 | 1.7E+08 | 3.0E+07 | 4.5E+08 |
| 10 | 2.5E+08 | 1.6E+08 | 2.0E+07 | 4.3E+08 |
| 11 | 2.2E+08 | 1.5E+08 | 3.0E+07 | 4.0E+08 |
| 12 | 2.0E+08 | 1.4E+08 | 3.0E+07 | 3.7E+08 |
| 13 | 1.6E+08 | 1.5E+08 | 2.0E+07 | 3.3E+08 |
| 14 | 1.5E+08 | 1.5E+08 | 2.0E+07 | 3.2E+08 |
| 15 | 1.5E+08 | 1.3E+08 | 2.0E+07 | 3.0E+08 |
| 16 | 1.4E+08 | 1.3E+08 | 2.0E+07 | 2.9E+08 |
| 17 | 1.2E+08 | 1.4E+08 | 2.0E+07 | 2.8E+08 |
| 18 | 6.0E+07 | 1.4E+08 | 1.0E+07 | 2.1E+08 |
| 19 | 4.0E+07 | 1.3E+08 | 2.0E+07 | 1.9E+08 |
| 20 | 3.0E+07 | 1.1E+08 | 2.0E+07 | 1.6E+08 |
| 21 | 4.0E+07 | 1.1E+08 | 2.0E+07 | 1.7E+08 |
| 22 | 1.0E+07 | 1.0E+08 | 1.0E+07 | 1.2E+08 |

E.f = *Enterococcus faecium*
L.p = *Lactobacillus plantarum*
L.c = *Lactobacillus casei*
LAB = Lactic Acid Bacteria
cfu per ml = colony forming units per millilitre

TABLE 2

Batch B (8060)

| Week | E.f | L.p | L.c | Total LAB |
|---|---|---|---|---|
| 0 | 3.0E+08 | 1.3E+08 | 1.5E+08 | 5.8E+08 |
| 1 | 3.6E+08 | 1.6E+08 | 2.5E+08 | 7.7E+08 |
| 2 | 3.0E+08 | 1.5E+08 | 1.4E+08 | 5.9E+08 |
| 3 | 1.8E+08 | 2.2E+08 | 1.2E+08 | 5.2E+08 |
| 4 | 2.1E+08 | 1.0E+08 | 8.0E+07 | 3.9E+08 |
| 5 | 1.7E+08 | 1.0E+08 | 7.0E+07 | 3.4E+08 |
| 6 | 1.6E+08 | 2.0E+08 | 8.0E+07 | 4.4E+08 |
| 7 | 1.5E+08 | 1.4E+08 | 7.0E+07 | 3.6E+08 |
| 8 | 1.2E+08 | 1.5E+08 | 5.0E+07 | 3.2E+08 |
| 9 | 1.5E+08 | 1.1E+08 | 6.0E+07 | 3.2E+08 |
| 10 | 2.3E+08 | 1.0E+08 | 5.0E+07 | 3.8E+08 |
| 11 | 1.8E+08 | 1.0E+08 | 2.0E+07 | 3.0E+08 |
| 12 | 1.6E+08 | 1.0E+08 | 3.0E+07 | 2.9E+08 |
| 13 | 1.2E+08 | 1.1E+08 | 3.0E+07 | 2.6E+08 |
| 14 | 1.0E+08 | 1.1E+08 | 2.0E+07 | 2.3E+08 |
| 15 | 1.0E+08 | 1.0E+08 | 2.0E+07 | 2.2E+08 |
| 16 | 1.0E+08 | 1.0E+08 | 2.0E+07 | 2.2E+08 |
| 17 | 8.00E+07 | 9.00E+07 | 1.00E+07 | 1.8E+08 |
| 18 | 9.00E+07 | 9.00E+07 | 1.00E+07 | 1.9E+08 |
| 19 | 8.00E+07 | 8.00E+07 | 2.00E+07 | 1.8E+08 |
| 20 | 6.00E+07 | 8.00E+07 | 1.00E+07 | 1.5E+08 |
| 21 | 5.00E+07 | 7.00E+07 | 1.00E+07 | 1.3E+08 |
| 22 | 4.00E+07 | 8.00E+07 | 1.00E+07 | 1.3E+08 |

EXAMPLE 5

Assessment of the Robustness of the Metabolically Active Culture and of Freeze-Dried Bacteria In this series of experiments a single strain of lactobacillus plantarum was used to inoculate growth media. Subsequent growth at about 37° C. was measured by monitoring absorbance at 600 nm (and also checked by plating out dilutions on agar media).

'Wet' refers to a liquid culture of the bacterium (produced by the method described in this patent application). 'Dry' refers to a lyophilised preparation of the bacterium, suspended in MRS broth (De Man, Rogosa and Sharpe Broth) just prior to incubation in the specified media. Identical numbers of viable 'wet' and 'dry' bacteria were used in each pair of incubations.

(1) Growth in a Rich and 'Friendly' Medium

Bacteria were inoculated into MRS broth and their growth monitored(x1=inoculum of $1 \times 10^7$ cfu/ml final concentration; x2=$2 \times 10^7$ cfu/ml). The results are shown in FIG. 1a. This first growth curve indicates that in a non-hostile environment, the liquid culture grows away faster than the lyophilised preparation. Presumably, the dormant bacteria in the lyophilised preparation need time to rehydrate and get their metabolism up and running.

(2) The Effect of Acid Shock

1% (v/v) of either a liquid culture, or a suspension of lyophilised bacteria, was added to MRS broth, which had been adjusted to various pH values with HCl. The bacteria were incubated in the acid broths for 1 hour and then samples were counted on MRS-agar plates.

| pH | 6 | 5 | 4 | 3 | 2 | 1 |
|---|---|---|---|---|---|---|
| Wet | $10^6$ cfu/ml | $10^6$ cfu/ml | $10^6$ cfu/ml | $10^6$ cfu/ml | $6 \times 10^5$ cfu/ml | 0 |
| Dry | $10^6$ cfu/ml | $10^6$ cfu/ml | $10^6$ cfu/ml | $2 \times 10^4$ cfu/ml | $1 \times 10^4$ cfu/ml | 0 |

Cfu = colony forming units per millilitre

This result indicates that the 'wet' bacteria are better able to survive the acidic environment than are the 'dry' bacteria. As the stomach may reach pH levels as low as 2, this is obviously relevant to survival and fitness of the bacteria during and following gastric transit.

(3) Combining the Effects of pH and Bile Salts

Figure 1B:
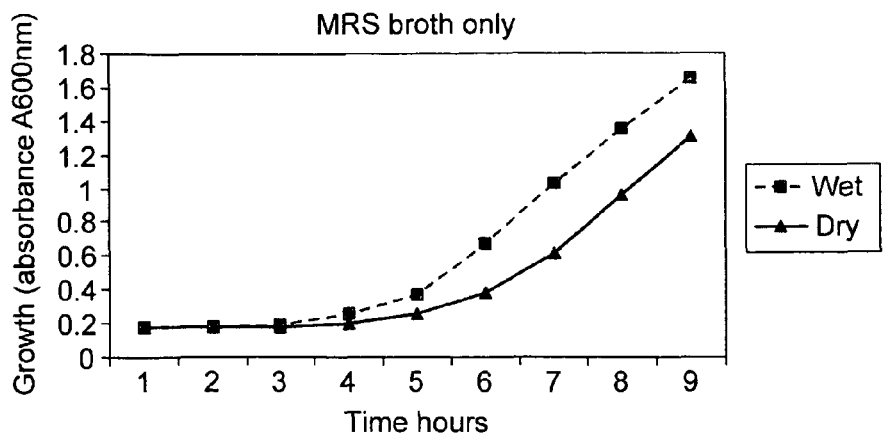
Figure 1C:
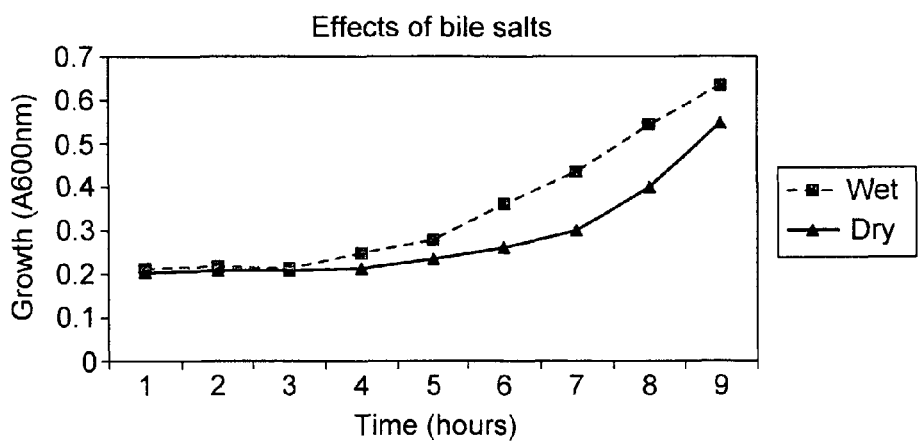
Figure 1D:
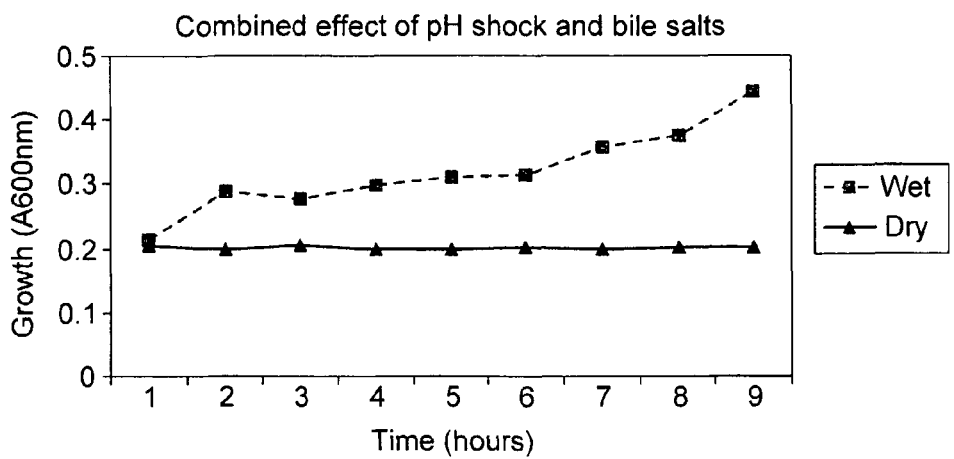

Taking the level of challenge a step further, the growth of 'wet' and 'dry' bacterial preparations was compared in the following conditions:

(a) MRS broth only (FIG. 1b)
b) MRS broth supplemented with 0.5% (w/v) bile salts (Oxoid L55)(FIG. 1c)
(c) Incubation in MRS at pH 3.0 for 1 hour, followed by growth in MRS-broth with bile salts (FIG. 1d).

The combined results from the experiments indicate the following points:

'Wet' bacteria grow faster than 'dry' bacteria.
Acid shock has a more detrimental effect on 'dry' bacteria than it does on 'wet.'
Bile salts inhibit both types, with possibly a more adverse effect on 'dry' than 'wet.'
The combined sequential effects of an acid shock followed by exposure to bile salts significantly slows the growth of 'wet' bacteria, but kills the 'dry' bacteria (judged by lack of colonies on agar plates).

However, whilst pH and bile tolerance are obviously important factors, there are a number of other challenges, both chemical and microbial, which probiotic bacteria must face. Thus the viability and total number of bacteria, as judged simply by the number of colony forming units per gram or ml, is only one indicator of the fitness of a preparation to function as a probiotic. If bacteria are not in an active state when entering the host, there is a significant possibility that they will either be killed, or pass too far along the digestive tract, before they have a chance to colonise. Therefore, probiotics are advantageous for use in a host if they are in a metabolically active state when entering the host. According to the invention, the bacteria are in a live and metabolically active form, such that they are able to withstand the hostile environment of the GI tract. The metabolically active nature of the product is designed to increase the chances of survival and colonisation within the host.

EXAMPLE 6

Affects on the Gut Microflora of Poultry Chicks

Figure 3:
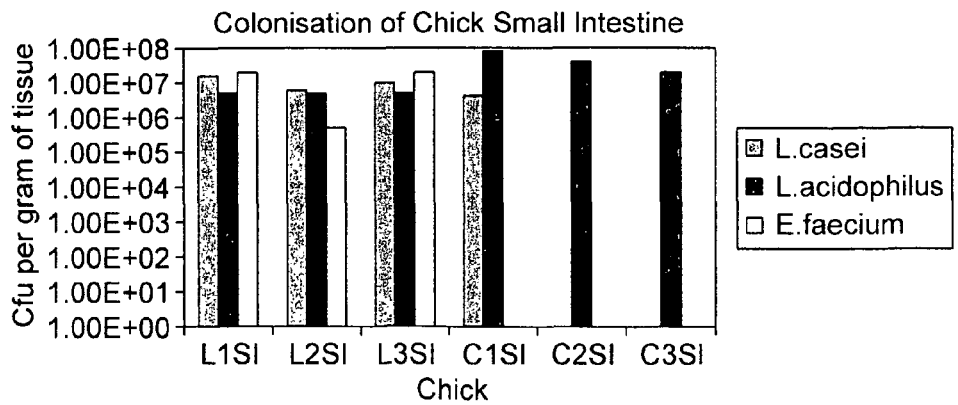
FIG. 3 shows the colonisation of bacteria in chick small intestine.

Introduction and Methods:
A probiotic containing the lactic acid bacteria *E. faecium*, *L. plantarum*, *L. casei* and *L. acidophilus* was prepared according to the method described herein. The probiotic was tested for its ability to alter the gut microflora of poultry chicks on a commercial poultry (broiler) unit.
Treatment of Chicks:
Poultry chicks were given the antibiotic Lincospectin from day 1 (day old) to day 3.
On day 4 the birds received no treatment.
On day 5, half of the broiler houses received the preparation at a rate of 1 litre per 5000 chicks The remaining houses were used as controls.
On day 6, six birds were randomly selected from each group, sacrificed, and the intestinal microflora examined. (Tissue samples from pairs of birds in each group were pooled, giving three samples from each group).
Microbiological Analysis:
The areas of the digestive system chosen for analysis is the upper intestinal tract, taken from the beginning of the small intestine down to the point of attachment of the yolk sac.
Gut tissues and contents from pairs of birds were macerated in sterile peptone water, diluted, and samples spread on a variety of semi-selective agars. Following incubation of the plates, colony characteristics and numbers were noted, together with microscopic analysis of the bacteria. Identity of lactic acid bacteria species was performed by examination of colony characteristic, cell morphology and carbohydrate fermentation profiles (the latter using the 'api 50 CH' test kit from BioMerieux).
Results:
The results are shown in FIG. 3.
L1 to L3=probiotic treated birds (pairs 1 to 3)
C1 to C3=Control birds (pairs 1 to 3)
S1=small intestine
cfu=colony forming units
As expected, there were many different microbes present in the gastrointestinal tracts of both control and probiotic-treated birds. Overall, there were similar numbers and types of bacteria in both groups of birds, but with some significant differences in the distribution and quantity of particular species.
Lactic Acid Bacteria
There was a very noticeable difference in the lactic acid bacteria (LAB) content between the preparation-treated and the control birds. Whilst both groups had comparable total numbers of LAB, the flora of the control birds was dominated by a single species, whereas the probiotic-treated birds had a broader mixture of species present.

EXAMPLE 7

Effect of Probiotic Preparation on Ostrich Chicks

A trial was carried out to evaluate the effects of a preparation according to the invention on ostrich chicks. The trial was carried out for a period of 4 weeks with chicks which suffer from diarrhoea from day 4. One group of chicks was treated with the preparation according to the invention, a second with an wide spectrum antibiotic and a third with a vitamin amino acid supplement. The trial results show that the group treated with the preparation according to the invention had a 67% decrease in mortality compared to the antibiotic treated group and that administration of the preparation could relive symptoms of constipation, diarrhoea, gut stases, deviant behaviour and prolapses. Furthermore, a weight increase of 27% compared to the control groups was observed in the group treated with the probiotic preparation.
In a second trial, wherein 100 ml of the preparation according to the invention was administered to breeder birds, it was observed that administration resulted in increased fertility compared to the control group.
Accordingly, these results show that the growth rate, morbidity and mortality is influenced by the administration of the probiotic preparation according to the invention.

EXAMPLE 8

Beneficial Effects of the Probiotic Preparation on Mammals

In a small independent trial, the effect of the preparation according to the invention on cats and dogs suffering from chronic enteritis was evaluated and it was found that it is useful in restoring a normal bowel flora.
In a trial in humans, volunteers have observed beneficial effects of the preparation to help with acute cases of diarrhea and to correct chronic bowel irregularity.
This pattern of benefits suggests that a product based on the method reported here could have significant benefits for humans in the control of both acute and chronic gastrointestinal dysfunction (including irritable bowel syndrome and inflammatory bowel disease, food poisoning, infectious diarrhea and constipation). A full clinical trial is also being carried out to support the results so far obtained.

REFERENCES

F. Fonseca, C. Béal, and G. Corrieu. *J. Dairy Res.* 67 (1):83-90, 2000.
M. L. F. Murga, A. P. D. Holgado, and G. F. de Valdez. *Cryobiology* 36 (4):315-319, 1998.
J. Hamilton-Miller. *Lancet* 355 (9201):413-414, 2000.
Kunze, W. Technology Brewing and Malting (1996)
Potential Health Benefits:
Collins, J. K., O'Sullivan, G. and Shanahan, F. (1996) *Gut flora and health—past, present and future*, Royal Society of Medicine Press Limited, London.
D. Haller, C. Bode, and W. P. Hammes. *Microbiol. Immunol.* 43 (10):925-935, 1999.
C. Hessle, L. Å. Hanson, and A. E. Wold. *Clin.Exp.Immunol.* 116 (2):276-282, 1999.
E. Isolauri, Y. Sütas, P. Kankaanpä, ä, H. Arvilommi, and S. Salminen. *Am.J.Clin.Nutr.* 73 (2):444S-450S, 2001.

M. Miettinen, S. Matikainen, J. Vuopio-Varkila, J. Pirhonen, K. Varkila, M. Kurimoto, and I. Julkunen. *Infect.Immun.* 66 (12):6058-6062, 1998.

A. E. Wold and I. Adlerberth. *Adv.Exp.Med.Biol.* 478:77-93, 2000.

Blood Chemistry

J. W. Anderson and S. E. Gilliland. *J.Am.Coll.Nutr.* 18 (1): 43-50, 1999.

H. Bukowska, J. Pieczul-Mróz, M. Jastrzebska, K. Chelstowski, and M. Naruszewicz. *Atherosclerosis* 137 (2): 437-438, 1998.

I. De Smet, P. De Boever, and W. Verstraete. *Br.J.Nutr.* 79 (2):185-194, 1998.

T. Endo, M. Nakano, S. Shimizu, M. Fukushima, and S. Miyoshi. *Biosci.Biotechnol.Biochem.* 63 (9):1569-1575, 1999.

H. Kikuchi-Hayakawa, N. Onodera, S. Matsubara, E. Yasuda, Y. Shimakawa, and F. Ishikawa. *Br.J.Nutr.* 79 (1):97-105, 1998.

H. Kikuchi-Hayakawa, H. Shibahara-Sone, K. Osada, N. Onodera-Masuoka, F. Ishikawa, and M. Watanuki. *Biosci.Biotechnol.Biochem.* 64 (3):466-475, 2000.

F. A. M. Klaver and R. van der Meer. The Assumed *Appl.Environ.Microbiol.* 59 (4):1120-1124, 1993.

B. K. Mital and S. K. Garg. *Crit.Rev.Microbiol.* 21 (3):175-214, 1995.

G. R. J. Taylor and C. M. Williams. *Br.J.Nutr.* 80 (4):S225-S230, 1998.

Cancer Treatment and Prevention

Y. Aso, H. Akaza, T. Kotake, T. Tsukamoto, K. Imai, and S. Naito. *Eur.Urol.* 27:104-109, 1995.

R. Balansky, B. Gyosheva, G. Ganchev, Z. Mircheva, S. Minkova, and G. Georgiev. *Cancer Lett.* 147 (1-2):125-137, 1999.

L. J. Brady, D. D. Gallaher, and F. F. Busta. *J.Nutr.* 130 (2):410S-414S, 2000.

D. D. Gallaher and J. Khil. *J.Nutr.* 129 (7):1483S-1487S, 1999.

B. R. Goldin. *Br.J.Nutr.* 80 (4):S203-S207, 1998.

S. L. Gorbach. *Am.J.Gastroenterol.* 95 (1):S2-S4, 2000.

K. Hirayama and J. Rafter. *Antonie Van Leeuwenhoek—International Journal of Microbiology* 76 (1):391-394, 1999.

K. Hirayama and J. Rafter. *Microbe.Infect.* 2 (6):681-686, 2000.

W. H. Ling. *Nutr.Res.* 15 (3):439-454, 1995.

G. H. McIntosh, P. J. Royle, and M. J. Playne. *Nutr.Cancer* 35 (2):153-159, 1999.

J. J. Rafter. *Scand.J.Gastroenterol.* 30:497-502, 1995.

B. S. Reddy. *Br.J.Nutr.* 80 (4):S219-S223, 1998.

Rowland, I. R. (1996) 'Gut microflora and cancer' in Leeds, A. R. and Rowland, I. R. (eds.) *Gut flora and health—past, present and future*, Royal Society of Medicine Press Limited, London.

M. D. Winters, T. L. Schlinke, W. A. Joyce, S. R. Glore, and M. M. Huycke. *Am.J.Gastroenterol.* 93 (12):2491-2500, 1998.

Diarrhoea and Constipation

T. Arvola, K. Laiho, S. Torkkeli, H. Mykkänen, S. Salminen, L. Maunula, and E. Isolauri. *Pediatrics* 104 (5):L1-L4, 1999.

R. Bennet, S. L. Gorbach, B. R. Goldin, T. W. Chang, B. E. Laughon, W. B. Greenough, and J. G. Bartlett. *Nutrition Today* 31 (6):35S-38S, 1996.

A. Bomba, R. Nemcová, S. Gancarciková, R. Herich, and R. Kastel. *Adv.Exp.Med.Biol.* 473:185-190, 1999.

N. M. De Roos and M. B. Katan. *Am.J.Clin.Nutr.* 71 (2):405-411, 2000.

H. L. DuPont. *J.Pediatr.* 134 (1):1-2, 1999.

S. L. Gorbach. *Am.J.Gastroenterol.* 95 (1):S2-S4, 2000.

M. Heyman. *J.Am.Coll.Nutr.* 19 (2):137S-146S, 2000.

E. Isolauri, M. Kaila, H. Mykkanan, W. H. Ling, and S. Salminen. *Dig.Dis.Sci.* 39 (12):2595-2600, 1994.

R. A. Oberhelman, E. H. Gilman, P. Sheen, D. N. Taylor, R. E. Black, L. Cabrera,. A. G. Lescano, R. Meza, and G. Madico. *J.Pediatr.* 134 (1):15-20, 1999.

R. D. Rolfe. *J.Nutr.* 130 (2):396S-402S, 2000.

J. Saavedra. *Am.J.Gastroenterol.* 95 (1):S16-S18, 2000.

C. Scarpignat .and P. Rampal. *Chemotherapy* 41 ((suppl 1)): 48-81, 1995.

A. V. Shornikova, I. A. Casas, H. Mykkänen, E. Salo, and T. Vesikari. *Pediatr.Infect.Dis.J.* 16 (12):1103-1107, 1997.

J. A. Vanderhoof, D. B. Whitney, D. L. Antonson, T. L. Hanner, J. V. Lupo, and R. J. Young. *J.Pediatr.* 135 (5):564-568, 1999.

Irritable Bowel Syndrome

P. Brigidi, B. Vitali, E. Swennen, G. Bazzocchi, and D. Matteuzzi. *Res.Microbiol.* 152 (8):735-741, 2001.

K. Niedzielin, H. Kordecki, and B. Birkenfeld. *Eur.J.Gastroenterol.Hepatol.* 13 (10):1143-1147, 2001.

S. Nobaek, M. L. Johansson, G. Molin, S. Ahrne, and B. Jeppsson. *Am.J.Gastroenterol.* 95 (5):1231-1238, 2000.

General Review:

Marteau, P. and Rambaud, J-C, (1996) 'Therapeutic applications of probiotics in humans' in Leeds, A. R. and Rowland, I. R. (eds.) *Gut flora and health—past, present and future*, Royal Society of Medicine Press Limited, London.

Stark, B. A. and Wilkinson, (eds.) (1989) Probiotics. Theory and *Applications, Chalcombe Publications, Bucks*, UK. 21

The invention claimed is:

1. A preparation comprising viable, metabolically active lactic acid bacteria and a growth substrate comprising a mixture of complex and simple sugars, proteins and peptides, wherein the bacteria in the preparation exhibit a near equilibrium growth state characterized in that the population of lactic acid bacteria are maintained at a constant level in the range of $10^8$ to $10^9$ viable cells per milliliter when stored at about 4° C. and at a controlled pH for a period of at least 5months, wherein the complex and simple sugars are present in the range of from 20 mg/ml to 40 mg/ml, and wherein the preparation has a total amount of reducing sugars in the range of from 5 mg/ml to 20.

2. The preparation of claim 1, wherein the total amount of reducing sugars is 10 mg/ml.

3. The preparation of claim 1, wherein the proteins and peptides are in a range of from 1 mg/ml to 2 mg/ml and wherein high molecular weight peptides are in a range of from 100 g/ml to 300 g/ml.

4. The preparation of claim 1, wherein the pH is controlled by the addition of a suitable buffer or combination of buffering agents, and buffering maintains the pH at a range from 3.8 to 4.5.

5. The preparation of claim 1, wherein the bacteria are of the genus *Lactobacillus*.

6. The preparation of claim 1, wherein the bacteria are of the genus *Enterococcus*.

7. The preparation of claim 1, wherein the bacteria are selected from the group consisting of at least one of *Enterococcus faecium, Lactobacillus plantarum, Lactobacillus casei* or *Lactobacillus acidophilus*.

8. The preparation of claim 1, wherein the bacteria are selected from the group consisting of at least one of *Enterococcus faecium, Lactobacillus plantarum* and *Lactobacillus casei*.

* * * * *

UNITED STATES PATENT AND TRADEMARK OFFICE
CERTIFICATE OF CORRECTION

PATENT NO. : 8,551,473 B2
APPLICATION NO. : 11/663877
DATED : October 8, 2013
INVENTOR(S) : Timothy Thurlby It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1904 days.

Signed and Sealed this

Fifteenth Day of September, 2015

Michelle K. Lee
*Director of the United States Patent and Trademark Office*